United States Patent [19]

Levy et al.

[11] Patent Number: 4,898,730
[45] Date of Patent: Feb. 6, 1990

[54] METHOD TO STIMULATE THE IMMUNE RESPONSE TO SPECIFIC ANTIGENS

[75] Inventors: Julia G. Levy, Vancouver; J. Kevin Steele, Victoria; Anthea T. Stammers, Port Coquitlan, all of Canada

[73] Assignee: The University of British Columbia, Vancouver, Canada

[21] Appl. No.: 25,463

[22] Filed: Mar. 13, 1987

[51] Int. Cl.$^4$ .................... A61K 39/00; A61K 45/02; A61K 37/02
[52] U.S. Cl. .................................... 424/88; 424/85.1; 424/89; 424/91; 424/92; 530/350; 530/351; 514/21
[58] Field of Search .................... 424/88, 85.1, 89, 91, 424/92; 530/351, 350; 514/21

[56] References Cited

U.S. PATENT DOCUMENTS 4,681,760  7/1987  Fathman ............................. 424/86
4,728,614  3/1988  Lau ..................................... 530/351

OTHER PUBLICATIONS

Green et al., "Contrasuppression in the mouse" Immunology Today, vol. 7, No. 3, pp. 81–86, 1986.
Green et al., "Hyperimmunity and the Decision to be Intolerent" Annals of the New York Acad. of Science, vol. 392, pp. 318–327, 1982.
Mattingly et al., "Immunologic Suppression After Oral Administration of Antigen", Journal of Immual., vol. 125, No. 3, pp. 1044–1047, 1980.
Suguimura et al., "Antigen-Specific T Cell Suppressor Factor (TSF): Isolation of a CDNA Clone Encoding for a Functional Polypeptide Chain of Phosphorylcholine Specific TSF", Eur. J. Immunol., vol. 15, pp. 873–880, 1985.
Germain et al., "Antigen-Specific T Cell-Mediated Suppression", II in Vitro Reduction by I-2 Coded L--Glutomic Acid-L-Tyrosine (GT) Specific T Cell Suppressor Factor (GT-T$_0$-F) of Suppressor T Cells (Ts$_2$) Bearing Distr at I-J-Determinants, Journal of Immunol., vol. 121, No. 2 pp. 602–607, 1978.
Germain et al., "Antigen Specific T Cell Mediated Suppression", Journal of Immunol., vol. 121, No. 2, pp. 608–612, 1978.
Green et al., (1982) Proc. Natl. Acad. Sci. (USA) 79, pp. 889–892.
Mattingly et al., (1978) J. Immunol 121:1878–1883.
Smith et al., (1982) J. Immunol 129:2332–2334.
Hamaoka et al., (1979) J. Exp. Med. 149:185–199.
Gershon et al., (1981) J Exp. Med. 153:1533–1546.
Green et al., (1982) Annals of the NY Acad, Sci. 392:318–327.
Green et al., (1986) Immunology Today 7:81–86.
Steele et al., (1985) J. Immunol. 134:2767–2778.
Steele et al., (1985) J. Immunol. 135:1201–1206
Steele et al., in *Induction and Recognition of the Transformed Cell* Greene, M. I. et al., eds., Plenum Press, New York, 1986, pp. 279–293.
Ptak et al., (1980) Nature 283:199–200.

Primary Examiner—Margaret Moskowitz
Assistant Examiner—Abdel A. Mohamed
Attorney, Agent, or Firm—Irell & Manella

[57] ABSTRACT

Factors secreted in the suppressor cascade are effective in contravening the suppression of the immune system in response to a particular antigen when properly administered. TsF2 factors may administered prior to or contemporaneously with the antigen; TsF1 factors, in order to exhibit this desired effect, must be administered prior to administration of antigen.

5 Claims, 2 Drawing Sheets

METHOD TO STIMULATE THE IMMUNE RESPONSE TO SPECIFIC ANTIGENS

TECHNICAL FIELD

The invention relates to the regulation of the immune system in response to specific antigens. In particular, the invention concerns stimulation of the immune response to these antigens by effecting contrasuppression.

BACKGROUND ART

In addition to raising the titers of specific antibodies secreted by the B-cell population, antigenic foreign substances stimulate responses from the lymphatic T-cell population. In general, there are now considered to be three subpopulations of T-cells-killer (or effector) cells, helper cells, and suppressor cells. Stated in a somewhat oversimplified manner, the helper cell population and the suppressor cell population exert the indicated opposite effects on the effectors and, in particular, on the formation and activity of cytotoxic T-lymphocytes (CTLs).

The suppressor cell population is considered to be to some degree self-regulating, i.e., to include cells which are contrasuppresive. Evidence for contrasuppresive cells has been shown by others, including the demonstration that these cells are involved in localizing the immune response in order to prevent unwanted reactions (Green, D. R., et al, *Proc Natl Acad Sci USA* (1982) 79: 889; Mattingly, J. A., et al, *J Immunol* (1978) 121: 1878. Countersuppressor cells have been implicated as a factor in autoimmune reactions such as in diabetes (Ptak, W., et al, *Nature* (1980) 283: 199); and in NZB mice (Smith, H. R., et al., *J Immunol* (1982) 129: 2332). It has also been shown that induction of contrasuppressor cells can be obtained by injection of hapten/IgG mixtures, leading to the destruction of tumors (Hamaoka, T., et al, *J Exp Med* (1979) 149: 185). Induction of contrasuppressors in vitro and in vivo has been demonstrated by preculturing with antigen alone or in combination with antibodies (Gershon, R. K., et al, *J Exp Med* (1981) 153: 1533; Green, D. R., et al, *NY Acad Sci* (1982) 398: 318; Green, D. R., et al, *Immunology Today* (1986) 7: 181).

A general model for suppressor T-Cell system is shown in the diagram below:

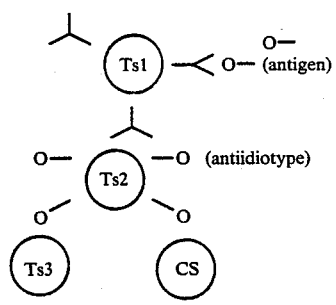

The end products of this cascade, designated in the diagram Ts3 and CS (contrasuppressors), presumably exert opposite effects. That is, the Ts3 cells are putatively effective in suppressing the immune response of the T-Cell system and the contrasuppressors regulate the activity of Ts3 either directly or indirectly. Both of these populations are in some way regulated by or interactive with the anti-idiotypic TsF2 factor secreted by the Ts2 cells of the cascade. The Ts2 cells are stimulated, in turn by TsF1 factors which are idiotypic and are secreted by Ts1 cells, the primary cells interactive with the stimulating antigen.

A murine hybridoma designated A10, which secretes a TsF1 factor in response to the P815 antigen of the corresponding murine tumor and which factor is specific for this antigen was described by Steele, J. K., et al, *J Immunol* (1985) 134: 2767-2778; and a human counterpart of this TsF1 factor has been found in tonsil cells (Steele, J. K., et al, *J Immunol* (1985) 135: 1201-1206). A hybridoma secreting a TsF1 specific for the antigen ferredoxin (Fd) is designated Fd11 and is described by Steele, J. K., et al, *J Immunol* (1986), in press. In addition, a TsF2-secreting cell line designated A29 which is anti-idiotypic with respect to the P815 antigen has also been described (Steele, J. K., et al, *J Immunol* (1986), in press.

It has also been previously shown that administration of the A10 generated TsF1 intravenously into mice contemporaneously with tumor cell injection enhances the in vivo growth of the P815 tumor specifically, and that the TsF1 is inhibitory to the development of P815-specific CTL's in vitro (Steele, J. K., et al, *J Immunol* (1985) 134: 2767-2778, supra); Steele, J. K., et al, in *Induction and Recognition of the Transformed Cell* (1986), Greene, M. I., et al, eds, Plenum Press, New York).

While the suppression of the immune system may be desirable in some cases, such as in the event of autoimmune disease or allergies, in most cases it is desirable to *stimulate* the ability of the immune system to cope with potentially harmful foreign material such as tumors and infectious organisms. Thus, it is particularly important that it has now been found that by correct timing of the administration of TsF1, rather than promoting the proliferation of invading tumors or pathogens, TsF1 enhances the effectiveness of the immune system against these invaders.

DISCLOSURE OF THE INVENTION

The invention provides methods to stimulate the immune response to specific foreign materials by modulation of the T-suppressor cell system. Administration of the appropriate TsF1 prior to exposure to the antigen-bearing foreign material, or administration of TsF2 in effective amounts enhances the immune response.

Thus, in one aspect, the invention relates to a method to stimulate a subject's immune response to a specific antigen which comprises administering to the subject, prior to exposure to the antigen, an effective amount of the antigen-specific TsF1. Adjuvant is not needed, and not desired if the effect is to be antigen-specific. In a second aspect, the invention relates to stimulating the immune system by administration of the corresponding anti-idiotypic TsF2. In other aspects, the invention relates to pharmaceutical compositions suitable for carrying out the method of the invention.

MODES OF CARRYING OUT THE INVENTION

Figure 1:
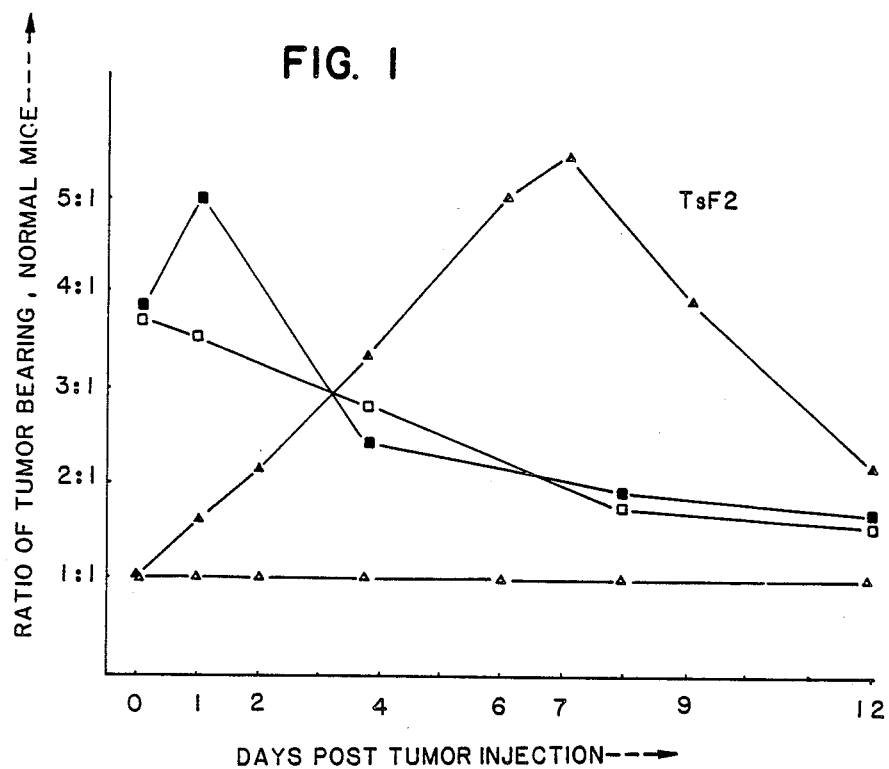
FIG. 1 shows the levels of TsF2 formed in response to tumor implantation depending on the pre-administration or not of TsF1.

The invention is directed to method to stimulate an immune response to a particular pathogen or tumor by pre-administration of the appropriate TsF1 factor. Thus, the method amounts to an immunization procedure and is thus indicated when exposure is expected. For example, immunization would be appropriate for travelers entering areas where organisms causing particular diseases, such as malaria, cholera, or yellow fever are known to be prevalent. Immunization would also be appropriate for persons perceived by genetic analysis or by family history to be susceptible to particular tumors. In order to have the desired effect, the TsF1 factor should be administered between 30 and 5 days prior to exposure preferably between 21 and 7 days, preferably around 14–10 days. The factor is injected or otherwise administered using approximately 0.1 μg–1 mg of purified TsF1 factor per kg body weight. For administration, the factors are formulated in a manner commonly utilized for administration of proteinaceous materials, but without the use of adjuvant. Typically, the proteins are administered I.V. and are formulated in, for example, phosphate buffered saline at physiological ionic strength, Ringer solution, Hank's solution and the like. Suitable formulations for such compounds can be found in *Remington's Pharmaceutical Sciences*, latest edition, Mack Publishing Company, Easton PA.

Injection of TsF2 need not be prior to exposure to antigen, but can be contemporaneous therewith. However, injection prior to exposure is also effective.

Suitable TsF1 and TsF2 factors can be obtained from immortalized cell lines using previously disclosed techniques, briefly described as follows.

In general, preparation of immortalized cell lines which secrete the desired factors utilizes immunization and immortalization techniques known in the art which are adapted to the purpose to be served by the invention. A subject mammal is immunized with the desired antigen and the spleen or peripheral blood lymphocytes immortalized, for example, according to the procedure of Kohler and Milstein or by infection with virus. The immortalized cells are then screened for production of the desired factors using an appropriate protocol. Cell lines obtained in this way are used as sources for the desired proteinaceous factor, which is secreted when the cells are cultured in vitro or grown as ascites tumors, as is understood in the art.

While the methods, therefore, to prepare hybridomas, or other immortalized cells, in general, are known, critical to obtaining the desired antigen-specific factors of the invention is the proper selection of immunogen and the proper design of a screening procedure for the factor-secreting immortalized cells that are prepared.

Using methods similar to those of Steele, J. K. et al (supra), any antigenic material can be used to stimulate the production of T cells secreting TsF1 factors specific for it; these factors are idiotypic (id+). These TsF1 factors can then be produced by immortalizing the appropriate T cells and screening for those which secrete the desired factor. The appropriate criteria for this screen are immunoreactivity with the antigen, combined with immunoreactivity with an antibody which is generically reactive with T cell suppressor factors.

Such antibodies are currently available. A particularly useful antibody is B16G (Maier, T. A., et al, *J Immunol* (1983) 131: 1843), which has been shown to be generically reactive to T suppressor factors, regardless of their antigen specificity, and can be obtained commercially from Quadra Logic Technologies, Vancouver, British Columbia.

The availability of antibodies useful for screening immortalized T cell populations for suppressor factors in general eases the production of any desired TsF1 component. Thus, a variety of such factors can be prepared so as to be immunoreactive with any desired antigen.

The TsF1 factors are also useful as immunogens for the production of the TsF2 factors, which are anti-idiotypic (id−). The procedure is analogous to that described above for preparation of TsF1. The other aspect critical for preparing the TsF2 factors is, of course, the choice of an appropriate screening procedure. Since the TsF2 factors are anti-idiotypic, they mimic the antigen. In addition they react with antibodies, such as B16G, which are generally reactive with T suppressor factors. In view of these two properties, a double criterion for screening is appropriate. The immortalized T cells obtained from animals immunized with the appropriate TsF1 are screened by choosing those which react both with the anti-suppressor factor antibody such as B16G and with an idiotypic antigen-specific factor. This factor would be either the appropriate TsF1 immunogen used to obtain the TsF2, or could also be B-cell-secreted antibodies raised to the original antigen. By using this combination of reactivities, only those T cells secreting the desired TsF2 factors are obtained.

The TsF1 factors generally have molecular weights of 80 kd to 90 kd and are composed of heterodimers with subunit molecular weights in the area of 45–50 kd with an associated peptide of approximately 25 kd. They are proteinaceous and heavily glycosylated. They react with antibodies generically specific for T-cell suppressor factors, and since they are antigen-specific idiotypes, they also react directly with the antigen. They do not react with antibodies raised against the antigen.

The TsF2 factors have molecular weights of approximately 70 kd. They are proteins, and may be glycosylated. Their properties are well defined. They are reactive with antibodies generically specific for T-cell suppressor factors, but they are antigen-specific. They are anti-idiotypes and therefore react with TsF1 specific to the antigen in question and with antibodies raised against that antigen. They do not bind to the antigen per se. These materials suppress the generation of cytotoxic lymphocytes specific to the antigen in in vitro assays and, further, remove factors from spleenocytes which suppress the formation of cytotoxic lymphocytes.

Thus, TsF1 and TsF2 factors related to any desired antigen can be prepared. Suitable antigens include antigenic factors associated with various bacteria such as Staphylococcus, Streptococcus, and *E. coli;* those associated with parasites such as malaria, and those associated with viruses such as hepatitis, herpes and the like.

EXAMPLE

The following example is intended to illustrate but by no means to limit the invention. The example sets forth experimental data obtained in mice which demonstrate the immune response-stimulating effect of P815 and ferredoxin TsF1 factors administered prior to antigen exposure, and of TsF2 factors administered at any time. While these data are demonstrative of the efficacy of these factors in murine systems, they indicate the universal application of this principle to vertebrate subjects in general, and to mammalian subject in particular. The cross-species reactivity of the factors is not at present known, and factors may or may not be transferable to closely related genetic species.

EXAMPLE 1

Materials and Methods

Female DBA/2 mice and CBAxDBA/2 F1 mice 6-8 weeks of age were used in all experiments; tumor cells were administered subcutaneously in PBS in the right flank at a concentration of $10^4$ cells in a volume of 200 $\mu$l.

Production of TsF1

The A10 and Fd11 TsF1's were produced by growing the hybridomas as an ascites tumor in CBAx DBA/2 F1 mice which received 0.5 ml of pristane 7 days earlier and 500 rads on the day of injection. Large numbers of cells ($>10^6$) were injected intraperitoneally, and cells for this purpose were maintained by passage in these animals. The ascites obtained was immediately diluted 5× in PBS, cells were removed by centrifugation, and the fluid was passed over immunoabsorbent columns of the B16G monoclonal linked to Sepharose 4B as described previously (Steele et al, *J Immunol* (1985) (supra)). Columns were washed in excess with PBS and adsorbed material was eluted with ice-cold 0.1N HCl. Eluted fractions were neutralized immediately and read for absorbance at 280 nm. Protein containing fractions were pooled, dialyzed against PBS and used for experimental purposes all within 24 h after removal of ascites. All procedures were carried out at 4° C. BW5147 (the T cell myeloma fusion partner for all herein cell lines, obtainable from ATCC) was used as a control.

Assays for TsF1 and TsF2 Production

Three selective immunoadsorbent columns were prepared by linkage of materials to cyanogen bromide activated Sepharose 4B. The materials included: the Mab B16G, P815 membrane extracts (both conjugated at 5.0 mg/ml beads), and the A10 TsF1 molecule purified as described above and conjugated at 1.0 mg/ml beads in PBS containing 4.0 mg/ml of bovine serum albumin. Control columns containing irrelevant Mab, and control ascites passed over B16G columns were also prepared.

A group of 25 mice were injected subcutaneously with $10^4$ P815 cells in 200 $\mu$l in the right flank. On days, 1, 2, 4, 6, 7, 9 and 12, three mice were sacrificed, and their spleens removed and pooled. Untreated control mice were treated in the same manner. Spleen cells were washed with PBS and solubilized using a standard lysis buffer 0.14M NaCl, 1.5 mM $MgCl_2$, 10 mM Tris HCl and 0.5% NP40 pH 8.6 in distilled $H_2O$).

Soluble materials from both tumor bearing and control mice were passed initially over a B16G immunoadsorbent, and reactive material was eluted with 0.1N HCl. Aliquots of each fraction (containing polyclonal TsF1) were titrated at doubling dilutions in bicarbonate coating buffer on ELISA plates. The remaining TsF1-containing eluates were then passed over P815 antigen columns, reactive material containing P815-specific TsF1 was eluted, and aliquots from each fraction from tumor bearing and normal mice were titrated on ELISA plates as described. Finally, remaining B16G eluted materials were passed over the A10 TsF1 immunoadsorbent column.

Reactive material (containing anti-idiotypic TsF2 components) was eluted and tested in the ELISA.

These procedures were repeated on all the days given above for both tumor bearing and control animals. ELISA plates were left for 18 h at 4° C. after coating and were developed using purified B16G Mab at a concentration of 10 $\mu$g/ml in PBS-Tween. Final development of plates was carried out using alkaline-phosphatase labeled rabbit anti-mouse Ig. Reactivity over background levels was determined by comparing the values obtained for materials from tumor bearing animals to the equivalent control value.

CTL Microassay

To assess the effects of the TsFs on CTLs, DBA/2 spleen cells were plated in doubling dilutions in V bottom plates (Linbro #76-023-05) from $10^6$ to $1.25 \times 10^5$ cells in 100 $\mu$l aliquots per well in replicates of 8. P815 cells were obtained from ascites fluid of DBA/2 mice, washed 3 times and incubated at 2 to $6 \times 10^6$ cells/ml with 50 $\mu$/ml mitomycin C in complete RPMI (RPMI, 10 mM Hepes, $5 \times 10^{-5}$M 2-mercaptoethanol, 10% FCS, penicillin/streptomycin) at 37° C. and 5% $CO_2$ for 1 h. P815 cells were then washed 3 times, resuspended in complete RPM1 and 100 $\mu$l containing $2.5 \times 10^4$ cells was added to all wells containing spleen cells. After 5 days incubation, cells were resuspended and 100 $\mu$l from all wells was transferred to U bottom plates (Linbro #76-24-205).

Fresh P815 cells were labeled for 1½ h with $^{51}Cr$ at $0.2$ mCi/$2 \times 10^6$ cells. The cells were washed, incubated at 37° and 5% $CO_2$ in complete RPMI for 3 to 4 hr. The labeled P815 cells were washed 3 times, resuspended in complete RPMI and 100 $\mu$l containing $10^4$ cells was added to all wells including 2 rows of 8 replicates of labeled P815 alone for calculation of spontaneous and maximum chromium release. The plates were centrifuged at 100 rpm for 5 min and then incubated at 37° C. and 5% $CO_2$. After 18 h, plates were again centrifuged and 100 $\mu$l of supernatant was removed from all wells except from one row of P815 cells alone in which 100 $\mu$l of cell suspension was removed to calculate maximum chromium release. Samples were counted in a Picker Pace 1 gamma counter. % specific lysis was calculated as follows:

$$\% \text{ specific lysis} = \frac{\text{sample cpm} - \text{spontaneous cpm}}{\text{maximum cpm} - \text{spontaneous cpm}} \times 100$$

EXAMPLE 2

The Effect of TsF1 Administration on Survival Time

The TsF1 factor from A10, affinity purified as described above, or control material were administered IV to DBA/2 mice in a total dosage of 20 $\mu$g at a time period between 7-14 days prior to tumor cell challenge with $10^4$ P18 815 cells injected subcutaneously. The result in terms of survival time are shown in Table 1.

| Experiment | Treatment | Time | Survival Time ± S.E.M. | p* |
|---|---|---|---|---|
| 1 | PBS | d-7, d-0 | 18.9 ± 0.61 | |
| | A10 | d-7, d-0 | 35.1 ± 3.14 | <0.001 |
| | A10 | d-14, d-7 | 34.9 ± 3.27 | <0.001 |
| 2 | BW5147 | d-14, d-7 | 23.3 ± 2.2 | |

-continued

| Experiment | Treatment | Time | Survival Time ± S.E.M. | p* |
|---|---|---|---|---|
| | A10 | d-14, d-7 | 38.0 ± 4.9 | <0.001 |
| 3** | PBS | d-10 | 21.6 ± 2.4 | |
| | A10 | d-10 | 36.4 ± 3.6 | <0.001 |
| | PBS | d 0 | 25.1 ± 3.6 | |
| | A10 | d 0 | 18.5 ± 1.6 | <0.05 |

*p values are from Students' t-test analyses of individual survival times of mice receiving A10 in comparison with appropriate control animals.
**In this experiment, affinity-purified A10 was administered to 16 animals, 8 of which were injected on the same day with P815, and 8 of which received P815 10 days later. Appropriate PBS-treated controls were maintained in both instances. Statistical analyses are based on comparison of A10-treated animals with their appropriate controls.

As shown in the table, the survival times were markedly increased when the A10-derived TsF1 factors were administered prior to the subcutaneous administration of tumor, but were decreased when administered contemporaneously.

EXAMPLE 3

Ability of Pre-Administered TsF1 to Regulate TsF2

The levels of TsF2 in membranes of treated and untreated animals were assessed as described in Example 1. In general, it was found that administration of TsF1 causes an increase in the level of TsF2. As the Ts2 cell population may be a target, as well as a downward participant in the suppressor cell cascade, diminution of TsF2 values may also be caused indirectly as a function of time by TsF1 injection.

Thus, as shown in FIG. 1, mice which received no TsF1 (triangles) experienced a dramatic rise in TsF2 levels over a period of 7 days following implantation of the tumor cells (solid triangles). Control animals (open triangles), of course, showed no change in TsF2. On the other hand, animals which had been treated on day −10 with TsF1 (20 μg/dose) had elevated TsF2 values at day 0, and in animals not implanted with tumors, the TsF2 level continued to decline. If tumor cells were implanted, an immediate rise in TsF2 levels was mitigated, so that by day 7 the levels of TsF2 approached those found in animals which received no tumor cells.

EXAMPLE 4

Ability of Pre-Administered TsF1 to Enhance CTL Production

Figure 2:
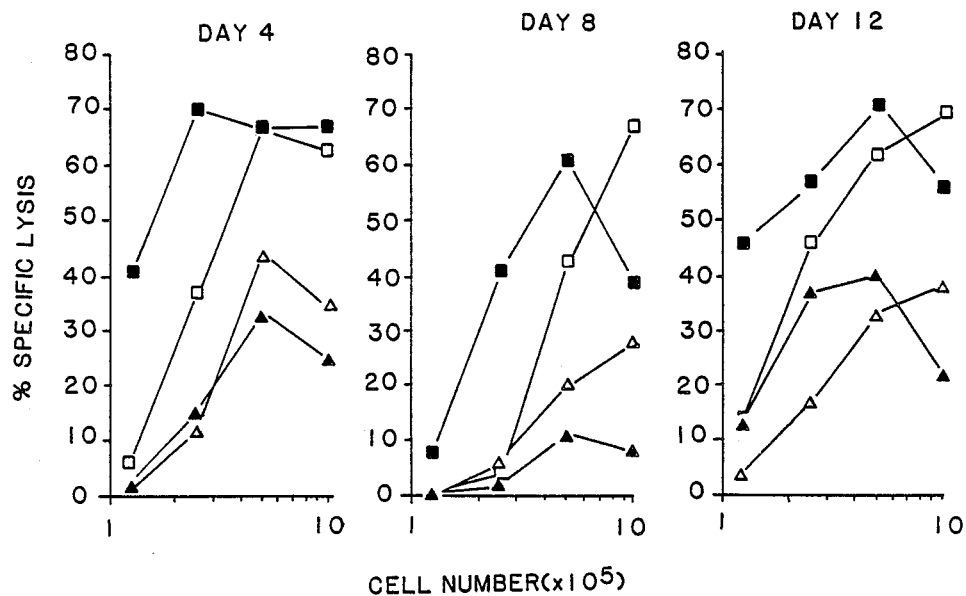
FIG. 2 shows the levels of CTLs in in vitro splenocyte cultures mixed with tumor cells taken from mice that were, or were not, pretreated with TsF1.

The production of P815-specific CTL in spleenocytes of DBA/2 mice cultured in vitro for 5 days with mitomycin C-treated P815 cells was measured as described in Example 1. The splenocytes were obtained from mice that had received no treatment (open triangles), received P815 on day 0 (open squares), received A10 (TsF1) on day −10 without (open squares), or with (closed squares), P815 on day 0. The results which showed that CTL activity was enhanced when TsF1 was applied on day −10. These results are shown in FIG. 2 for levels of CTL measured on days 4, 8, and 12. As expected, cultures not exposed to tumor cells (open squares and triangles) always showed lower CTL levels than those exposed. The highest levels were attained for those cultures treated with the P815-specific TsF1 at day −10 (closed squares). As shown in FIG. 2, in general, administration of TsF1 causes an increase in CTL performance in vitro.

EXAMPLE 5

The specificity of the response to TsF1s associated with a particular antigen was demonstrated in vivo using formation of antibody as a criterion.

DBA/2 mice received 20 μg of affinity purified Fd11 TsF1 or A10 TsF1, or PBS intravenously. They were rested for 10 days following which they were immunized with both Fd and KLH (20 μg each) emulsified in 50% complete Freunds' adjuvant (day 0) subcutaneously. They were bled on day 21, boosted in the same manner on day 28 bled again on day 35. Their serum was tested in a standard ELISA for the presence of antibodies to both Fd and KLH as described previously.

Since DBA/2 mice are absolute nonresponders to ferredoxin, as are all $H-2^D$ mice, normally it would be expected that no antibody to ferredoxin would result. The results of this assay showed that TsF1, as secreted by the Fd11 cell line when administered on day −10, converted the DBA/2 mice to responder status to ferredoxin, but had no effect on the KLH response; administration of A10 had no effect on either response.

We claim:

1. A method to enhance the immune response to a specified antigen which comprises administering to a mammal in need of such treatment at a time prior to exposure to said antigen effective to enhance immune response upon exposure to said antigen, an amount of an idiotypic factor secreted by Ts1 cells (TsF1) immunoreactive with the antigen effective to enhance said immune response.

2. The method of claim 1 wherein the antigen is a tumor antigen.

3. The method of claim 1 wherein the time prior to exposure is between 30 and 5 days.

4. The method of claim 1 wherein the time prior to exposure is between 21 and 7 days.

5. A pharmaceutical composition suitable to the method of claim 1 which comprises amount of TsF1 immunoreactive with a specified antigen effective to enhance immune response to said antigen in admixture with a pharmaceutically acceptable excipient.

* * * * *